US012734119B2

(12) United States Patent
Kim et al.

(10) Patent No.: US 12,734,119 B2
(45) Date of Patent: Sep. 15, 2026

(54) COMPOSITION FOR ANTI-AGING OR SKIN REGENERATION COMPRISING ISOPROCURCUMENOL

(71) Applicants: POSCO CO., LTD, Pohang-si (KR); POSTECH Research and Business Development Foundation, Pohang-si (KR); RESEARCH INSTITUTE OF INDUSTRIAL SCIENCE & TECHNOLOGY, Pohang-si (KR)

(72) Inventors: Kyong-Tai Kim, Pohang-si (KR); Kwang-Ho Kwon, Pohang-si (KR); Sung-Wook Kim, Pohang-si (KR); Sung-Woo Jeong, Jinju-si (KR)

(73) Assignees: POSCO CO., LTD, Pohang-si (KR); POSTECH Research and Business Development Foundation, Pohang-si (KR); RESEARCH INSTITUTE OF INDUSTRIAL SCIENCE & TECHNOLOGY, Pohang-si (KR)

( * ) Notice: Subject to any disclaimer, the term of this patent is extended or adjusted under 35 U.S.C. 154(b) by 515 days.

(21) Appl. No.: 18/023,956

(22) PCT Filed: Aug. 27, 2021

(86) PCT No.: PCT/KR2021/011529

§ 371 (c)(1),
(2) Date: Feb. 28, 2023

(87) PCT Pub. No.: WO2022/045833

PCT Pub. Date: Mar. 3, 2022

(65) Prior Publication Data

US 2023/0320957 A1 Oct. 12, 2023

(30) Foreign Application Priority Data

Aug. 28, 2020 (KR) ........................ 10-2020-0109404

(51) Int. Cl.
*A61K 8/35* (2006.01)
*A61K 31/122* (2006.01)
*A61Q 17/04* (2006.01)
*A61Q 19/08* (2006.01)

(52) U.S. Cl.
CPC .............. *A61K 8/35* (2013.01); *A61K 31/122* (2013.01); *A61Q 17/04* (2013.01); *A61Q 19/08* (2013.01)

(58) Field of Classification Search
CPC ........................................................ A61K 8/35
See application file for complete search history.

(56) References Cited

U.S. PATENT DOCUMENTS

2007/0243132 A1 10/2007 Russell-Jones et al.
2021/0093529 A1* 4/2021 LaRosa .................. A61K 8/445
2021/0100728 A1 4/2021 Kim et al.

FOREIGN PATENT DOCUMENTS

CN 107753852 A * 10/2017
CN 111315377 A 6/2020
KR 10-2004-0073478 A 8/2004
KR 10-2009-0007564 A 1/2009
KR 10-2011-0061960 A 6/2011
KR 10-2019-0014340 A 2/2019
KR 10-2093884 B1 3/2020
WO 03/051380 A2 6/2003
WO 2007/109210 A2 9/2007
WO WO2017/142158 * 8/2017

OTHER PUBLICATIONS

Ohshiro et al. Structures of Sesquiterpenes from Curcuma Longa (Year: 1989).*
Cleveland Clinic. Sun-Damaged Skin (Photoaging). (Year: 2025).*
Sumiyoshi et al. Effects of a turmeric extract (*Curcuma longa*) on chronic ultraviolet B irradiation-induced skin damage in melanin-possessing hairless mice. (Year: 2009).*
Li et al. Chemical compoistion and product quality control of turmeric (*Curcuma longa*)). (Year: 2011).*
Communication dated Aug. 12, 2024 issued by the State Intellectual Property Office of the P.R.China in application No. 202180052690.3.
Jin Zhehu, et al., "Dermatovenerology", People's Military Medical Press, Edition 1, Feb. 2013, p. 277 (3 pages total).
Tae Kyoung Lee, et al., "Bioactivity-based analysis and chemical characterization of anti-inflammatory compounds from *Curcuma zedoaria* rhizomes using LPS-stimulated RAW264.7 cells", Bioorganic Chemistry, vol. 82, 2019, pp. 26-32.
Hui Yongzheng, "Comprehensive Natural Products in Traditional Chinese Medicine V", Shanghai Scientific & Technical Publishers, 2011, p. 3881 (3 pages total).
Zhang Guoan, "General Practice of Diagnosis and Treatment in the Department of Burns", China Medical Science Press, 2012, Edition 1, p. 23 (3 pages total).
"Paper Collection in the Meeting of Chinese Aesthetic and Plastic Physicians, the Working Conference of Special Field Meeting 2005", Chinese Medical Doctor Association, 2005, p. 217 (4 pages total).
Office Action issued Mar. 31, 2025 in Chinese Patent Application No. 202180052690.3.
Omer Hamdi et al., "Neuroprotective and Antioxidant Constituents from Curcuma zedoaria Rhizomes", Records of Natural Products, 2015, pp. 349-355, vol. 9, No. 3.
Aknarin Pintatum et al., "In Vitro Anti Inflammatory, Anti-Oxidant, and Cytotoxic Activities of Four *Curcuma* Species and the Isolation of Compounds from Curcuma aromatica Rhizome", Biomolecules, May 21, 2020, pp. 1-14, vol. 10, No. 799.

(Continued)

*Primary Examiner* — Sarah Alawadi
(74) *Attorney, Agent, or Firm* — Sughrue Mion, PLLC

(57) ABSTRACT

Disclosed is a composition for anti-aging or skin regeneration comprising Isoprocurcumenol, and use of Isoprocurcumenol or a salt thereof and, more particularly, to a composition for anti-aging or skin regeneration comprising Isoprocurcumenol represented by the following formula (1) or a salt thereof, and use of Isoprocurcumenol or a salt thereof.

7 Claims, 6 Drawing Sheets

(56) References Cited

OTHER PUBLICATIONS

Rabia F. El-Hawaz, "In vitro mineral nutrition of *Curcuma longa* L. affects production of volatile compounds in rhizomes after transfer to the greenhouse", BMC Plant Biology, 2018, pp. 1-13, vol. 18, No. 122.
Eun Bee Jung et al., "Curcuzedoalide contributes to the cytotoxicity of Curcuma zedoaria rhizomes against human gastric cancer AGS cells through induction of apoptosis", Journal of Ethnopharmacology, 2018, pp. 48-55, vol. 213.
International Search Report for PCT/KR2021/011529 dated, Dec. 14, 2021 (PCT/ISA/210).

* cited by examiner

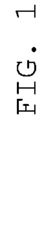
FIG. 1
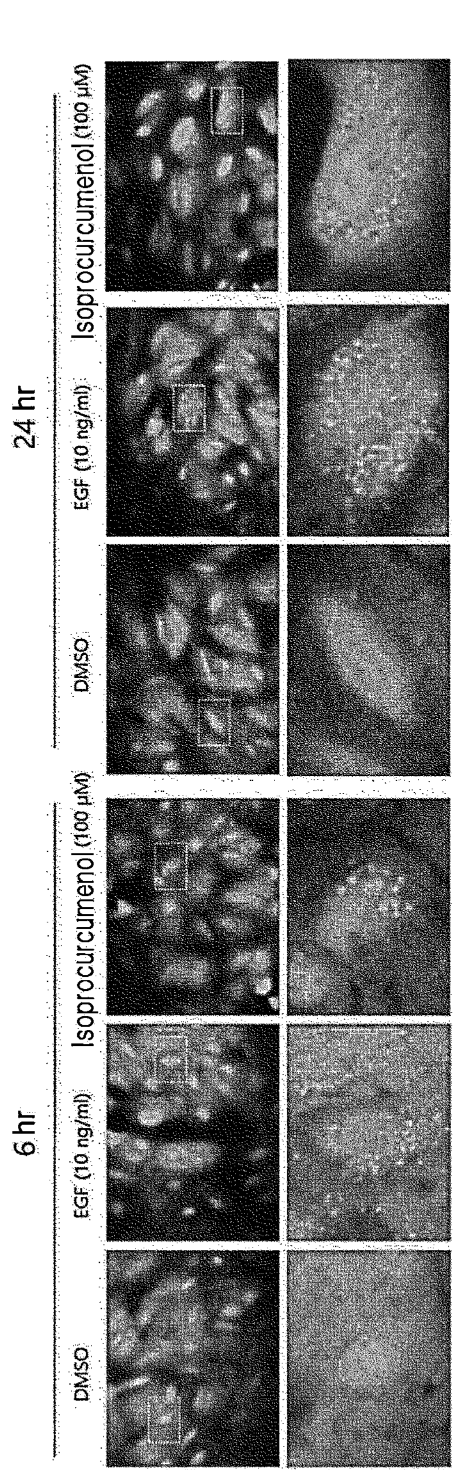

COMPOSITION FOR ANTI-AGING OR SKIN REGENERATION COMPRISING ISOPROCURCUMENOL

CROSS REFERENCE TO RELATED APPLICATIONS

This application is a National Stage of International Application No. PCT/KR2021/011529 filed Aug. 27, 2021, claiming priority based on Korean Patent Application No. 10-2020-0109404 filed Aug. 28, 2020, the entire disclosures of which are incorporated herein by reference.

TECHNICAL FIELD

The present invention relates to a composition for anti-aging or skin regeneration and, more particularly, to a composition for anti-aging or skin regeneration comprising Isoprocurcumenol.

BACKGROUND ART

Aging of skin is an inevitable phenomenon. Aging causes loss of skin elasticity, creates wrinkles and causes symptoms such as pigmentation and dermal atrophy. Aging of skin is largely divided into physiological aging, which indicates changes in the function, structure and shape of the skin, and aging caused by external stimuli such as ultraviolet rays.

As skin ages, the function of cells decreases, and, at the same time, skin is affected by the external environment such as ultraviolet rays. First, as aging progresses, the division rate of keratinocytes slows down. Although the normal skin regeneration cycle is about 28 days, this cycle increases with aging. Next, the number of fibroblasts known to exist in the dermal layer decreases with aging, and, at the same time, the function decreases. Fibroblasts are cells that produce collagen and elastin fibers to provide elasticity to the skin. However, when the number of the fibroblasts decreases and their function decreases, the atrophy of the dermis occurs. Finally, the expression of matrix proteases increases with aging. Therefore, collagen and elastin fibers are decomposed by the matrix proteases, resulting in an increase in the atrophy of the dermis.

However, even if aging cannot be completely prevented in the age of 100 years of life, expectations and demand for substances that can improve skin aging to enhance beauty are increasing. Therefore, substances that slow or improve skin aging need to be rapidly developed.

An epidermal growth factor (EGF) is a growth factor that regulates the growth and survival of epidermal or epidermal cells. The EGF is also known as a factor related to cancer and has been used medically for the treatment of wounds and burns. Recently, the EGF has been widely used as a raw material for cosmetics, and many studies such as Korean Patent No. 2093884 have been conducted on cosmetic compositions for preventing skin aging, comprising the EGF. Therefore, there is a need for research on naturally-derived small molecule substances that have a function similar to that of the EGF and are stable and useful for passing through the skin barrier. However, it is known that biosynthesis, separation and purification of the EGF are costly, and it is difficult to store the EGF in an active state. In addition, there is a problem in that the EGF cannot easily pass through the skin barrier due to its large molecular weight.

Therefore, there is a need for research on naturally-derived small molecule substances that have a function similar to that of the EGF and are stable and useful for passing through the skin barrier.

SUMMARY OF INVENTION

Technical Problem

An aspect of the present disclosure is to provide a composition for anti-aging or skin regeneration comprising Isoprocurcumenol which is a naturally-derived small molecule substance, or a salt thereof, as an active ingredient in order to provide a composition for anti-aging or skin regeneration that has a function similar to that of the EGF and is stable and useful for passing through the skin barrier.

Solution to Problem

According to an aspect of the present disclosure, the present invention provides a composition for anti-aging or skin regeneration comprising, as an active ingredient, Isoprocurcumenol represented by the following formula (1) or a salt thereof:

[Formula (1)]

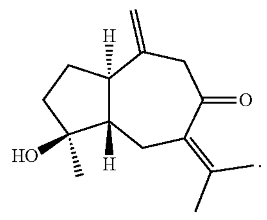

Advantageous Effects of Invention

According to an aspect of the present disclosure, Isoprocurcumenol may be extracted from various plant species such as *zedoaria*. The composition according to the present invention has the advantage of not having side effects by using same. In addition, Isoprocurcumenol, like an EGF, binds to an EGFR to activate signals related to the survival, growth and proliferation of cells, thereby increasing the resistance and viability of skin cells from external stimuli and enhancing regeneration of skin damaged by external stimuli or aging. Moreover, although Isoprocurcumenol has a function similar to that of the EGF, unlike the EGF, it is stable and small in size and, thus, has the advantage of being able to move through the skin barrier to the skin base layer to perform the function. Therefore, Isoprocurcumenol of the present invention may be used in various ways, for example, in drugs, quasi-drugs, cosmetics, fragrance materials, functional bio materials and functional food materials.

BRIEF DESCRIPTION OF DRAWINGS

FIG. 1 shows the results of confirming that, in the expression of a biosensor protein (EGFP-SH2) by intracellular injection of an EGFR activity measurement biosensor system, the protein was expressed by an EGF and further by Isoprocurcumenol.

BEST MODE FOR INVENTION

Figure 2:
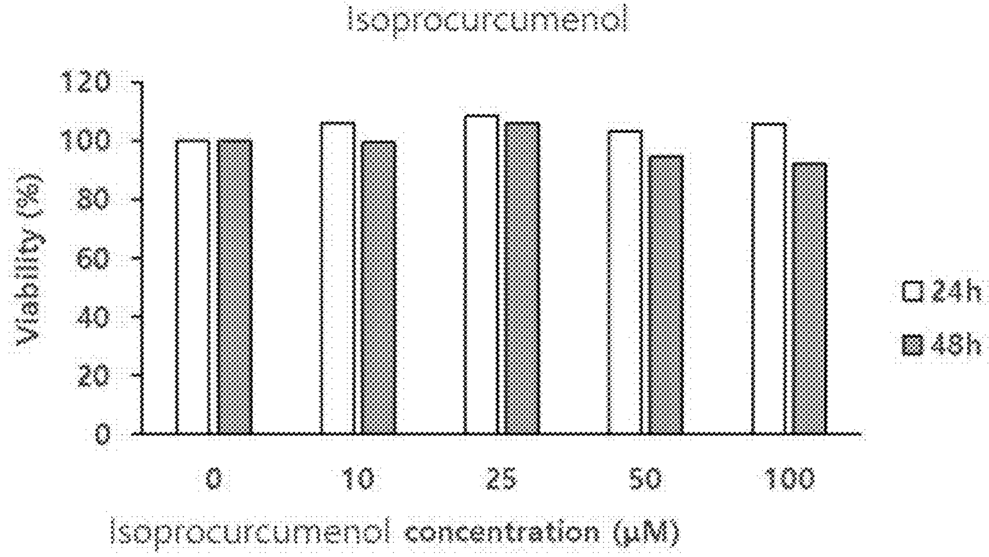
FIG. 2 shows the results of confirming cytotoxicity on HaCaT cells as keratinocytes depending on the concentrations of Isoprocurcumenol.

Hereinafter, preferred embodiments of the present invention will be described with reference to the attached drawings. However, the embodiments of the present invention may be modified into various forms, and the scope of the present invention is not limited to the embodiments described below.

The inventors have completed the present invention by experimentally confirming that Isoprocurcumenol, as a naturally-derived small molecular substance, has a function similar to that of an epidermal growth factor (EGF) and is stable and small in size to easily move through the skin barrier.

The present invention relates to the use of Isoprocurcumenol represented by the following formula (1) or a salt thereof for the preparation of a composition for anti-aging or skin regeneration:

[Formula (1)]

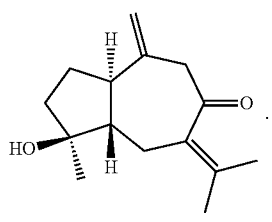

Specifically, the present invention provides a composition for anti-aging or skin regeneration, comprising, as an active ingredient, Isoprocurcumenol represented by the following formula (1) or a salt thereof:

[Formula (1)]

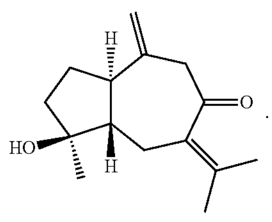

The Isoprocurcumenol, i.e., 2',3,3',4,4'-pentahydroxychalcone, may be obtained from extracts of various plant species such as *zedoaria* and has a function similar to that of an epidermal growth factor (EGF) that activates signals related to the survival, growth and proliferation of cells in the cells, thereby increasing the resistance and viability of skin cells from external stimuli and enhancing regeneration of skin damaged by external stimuli or aging.

The composition of the present invention may comprise the Isoprocurcumenol or a salt thereof in an amount of 10 nM to 100 μM, or 1 to 100 μM, for example, 5 to 100 μM, preferably 10 to 100 μM, and more preferably 25 to 50 μM. When the concentration of the Isoprocurcumenol or a salt thereof is less than 1 μM, the effect of the Isoprocurcumenol or a salt thereof may not be sufficiently expressed, and, when the concentration is more than 100 μM, cytotoxicity may significantly increase.

"Skin regeneration" of the present invention may refer to the promotion of the growth of skin cells and enhancement of the viability to prevent cell damage from external or internal stimuli, decrease of skin wrinkles and enhancement of the elasticity of skin. In addition, the skin regeneration includes the meaning of the improvement or treatment of skin damage caused by external environment, such as skin and tissue damage caused by burns. As such, the composition of the present invention may improve or treat burn wounds.

Moreover, the Isoprocurcumenol or a salt thereof of the present invention may bind to an EGFR to promote cell proliferation or growth, thereby activating anti-aging or skin regeneration. The cell proliferated or grown by the Isoprocurcumenol or a salt thereof of the present invention may be an epidermal cell, preferably a keratinocyte, which is a keratin-producing cell, but the present invention is not limited thereto.

Keratin, as a protein that makes up the main composition of various tissues in an animal, makes the hair glossy and elastic and gives life and elasticity to the skin. In addition, a keratin protein in the corneum of skin has strong resistance to chemicals so as to perform a protective function against chemical irritation to the skin.

Accordingly, the composition of the present invention may enhance skin elasticity or improve the problem of skin wrinkles.

Meanwhile, the composition of the present invention may enhance resistance to cell damage due to external stimuli, thereby preventing or improving cell damage due to external stimuli. The external stimuli may be chemical stimuli by a cosmetic or other external agent, physical stimuli, or ultraviolet rays, preferably ultraviolet rays, but the present invention is not limited thereto.

Moreover, the composition of the present invention may be a parenteral or an oral composition, for example, a pharmaceutical composition, a cosmetic composition, or a health functional food composition.

Specifically, when the composition of the present invention is a pharmaceutical composition, the composition may additionally comprise a pharmaceutically acceptable carrier, and the composition may additionally comprise an appropriate carrier, template, and diluent commonly used in the preparation of a pharmaceutical composition. The composition may also be formulated and used in the form of an oral formulation, an external preparation, a suppository (e.g., powder, granules, a tablet, a capsule, a suspension, an emulsion, a syrup and an aerosol) and a sterile injectable according to a method conventionally known in the art.

The pharmaceutical composition according to the present invention may be formulated and used in the form of an external preparation (e.g., powder, granules, a tablet, a capsule, a suspension, an emulsion, a syrup and an aerosol) and a sterile injectable and may preferably have a formulation of a cream, a gel, a patch, a sprayer, an ointment, an emplastrum, a lotion, a liniment, a paster or a cataplasma. The carriers, excipients and diluents that may be contained in the composition may be a compound comprising at least one of lactose, dextrose, sucrose, oligosaccharide, solbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate and mineral oil.

The composition may be prepared using a diluent or an excipient (e.g., a filler, an extender, a binder, a wetting agent, a disintegrating agent and a surfactant). For example, solids for oral administration comprise tablets, pills, powders, granules, capsules, etc., and such solids may be prepared by mixing the extract with at least one excipient (e.g., starch, calcium carbonate, sucrose, lactose and gelatin). In addition to simple excipients, lubricants such as magnesium stearate talc may also be used. Liquid preparations for oral use (e.g., a suspension, a solution, an emulsion and a syrup) may comprise various excipients (e.g., wetting agents, sweeteners, air fresheners and preservatives), in addition to simple diluents such as water and liquid paraffin commonly used in the art.

Preparations for parenteral administration may comprise sterilized aqueous solutions, non-aqueous solvents, suspensions, emulsions, lyophilized agents and suppositories. The non-aqueous solvents and suspensions may comprise propylene glycol, polyethylene glycol, vegetable oil such as olive oil, and an injectable ester such as ethylolate. Witepsol, macrogol, Tween 61, Cacao butter, laurin, glycerogelatin, etc. may be used as a base for the suppositories.

The pharmaceutical composition according to the present invention may be administered in a pharmaceutically effective amount. In the present invention, “a pharmacologically effective amount” refers to an amount sufficient to treat a disease at a reasonable rate of benefit/risk applicable to medical treatment. The effective dose level may be determined according to the type and severity of the patient’s disease, the activities of the drug, the sensitivity to the drug, the duration and route of administration, and the rate of excretion, the time period of treatment, factors such as drugs used concurrently, and other factors well known in the medical field.

The pharmaceutical composition according to the present invention may be administered as a single therapeutic agent or in combination with other therapeutic agents, may be administered sequentially or simultaneously with conventional therapeutic agents, and may be administered single or multiple times. It is important to administer the minimum amount which may obtain the maximum effect without causing side effects, in view of all of the above factors. Such amount may be easily determined by a person skilled in the art to which the present invention belongs.

The pharmaceutical composition of the present invention may be administered to a subject by various routes. The pharmaceutical composition of the present invention is determined according to various factors (e.g., a disease to be treated, the route of administration, patient’s age, sex and weight, and severity of the disease) and the type of a drug as an active ingredient.

The composition of the present invention may be provided in the form of a health functional food composition. In addition, the composition may be added to food for the purpose of skin regeneration (e.g., anti-aging, enhancement of skin elasticity and improvement of the problem of skin wrinkles). The health functional food composition according to the present invention may be used as it is or used together with other foods or food ingredients, and may be appropriately used according to a conventional method. The amount of an active ingredient to be mixed may be suitably determined depending on the intended use such as prevention and health or therapeutic treatment. When preparing a food or a beverage, Isoprocurcumenol or a salt thereof may generally be added to the health functional food composition according to the present invention in an amount of greater than 0 and up to 15% by weight, preferably 1 to 10% by weight or less, based on the weight of the total composition. However, the Isoprocurcumenol has no problem in terms of stability and, thus, may be used as an active ingredient in an amount equal to or greater than the above range.

The type of the food is not particularly limited, but examples of a food that may comprise the material are meat, sausage, bread, chocolate, candies, snacks, confectionery, pizza, ramen, other noodles, gums, and dairy products including ice creams, various soups, beverages, tea, drinks, vitamin complexes, etc., and may comprise all health functional foods in a conventional sense.

The beverages, like conventional beverages, may comprise various flavoring agents or natural carbohydrates as additional ingredients. The natural carbohydrates are monosaccharides such as glucose and fructose, disaccharides such as maltose and sucrose, polysaccharides such as dextrin and cyclodextrin, and sugar alcohols such as xylitol, sorbitol and erythritol. The sweetener may comprise natural sweeteners such as thaumatin and stevia extract, or synthetic sweeteners such as saccharin and aspartame. The amount of the natural carbohydrates may be about 0.01 to 0.20 g, preferably about 0.04 to 0.10 g, per 100 mL of the health functional food composition according to the present invention.

In addition, the health functional food composition according to the present invention may comprise various nutritional supplements, vitamins, electrolytes, flavoring agents, colorants, pectic acids and salt thereof, alginic acids and salt thereof, organic acids, protective colloidal thickeners, pH regulators, stabilizers, preservatives, glycerin, carbonating agents used in carbonated beverages, etc. Moreover, the health functional food composition according to the present invention may comprise fruit flesh for preparing natural fruit juice, fruit juice beverages and vegetable beverages. These components may be used independently or in combination. The amount of these additives is not very important, but may be selected in the range of 0.01 to 0.20 parts by weight per 100 parts by weight of the health functional food composition according to the present invention.

The composition of the present invention may be provided in the form of a cosmetic composition. The formulation of the cosmetic composition according to the present invention may be in the form of a skin lotion, a skin softener, a skin toner, an astringent, a lotion, a milky lotion, a moisturizing lotion, a nourishing lotion, a massage cream, a nourishing cream, a moisturizing cream, a hand cream, a foundation, an essence, a nourishing essence, a pack, a soap, a cleansing foam, a cleansing lotion, a cleansing cream, a body lotion or a body cleanser.

The cosmetic composition according to the present invention may additionally comprise a compound selected from the group consisting of water-soluble vitamins, oil-soluble vitamins, high-molecular peptides, high-molecular polysaccharides and sphingolipids.

Any water-soluble vitamins may be used as long as they may be added to a cosmetic composition. Preferably, vitamin B1, vitamin B2, vitamin B6, pyridoxine, pyridoxine hydrochloride, vitamin B12, pantothenic acid, nicotinic acid, nicotinic acid amide, folic acid, vitamin C, vitamin H, etc. may be used. The salt thereof (e.g., thiamin hydrochloride and ascorbic acid sodium salt) or derivatives thereof (e.g., ascorbic acid-2-phosphate sodium salt and ascorbic acid-2-phosphate magnesium salt) may also be used as water-soluble vitamins in the present invention. The water-soluble vitamins may be obtained by conventional methods (e.g., a microbial transformation method, a purification method from a microbial culture and an enzymatic or a chemical synthesis method).

Any useful vitamins may be used as long as they may be added to cosmetics and preferably comprise vitamin A, carotene, vitamin D2, vitamin D3, vitamin E (e.g., dl-alpha tocopherol, d-alpha tocopherol and d-alpha tocopherol), etc. The derivatives thereof (e.g., ascorbine palmitate, ascorbine stearate, ascorbine dipalmitate, dl-alpha tocopherol acetate, dl-alpha tocopherol nicotinate, vitamin E, DL-pantothenyl alcohol, D-pantothenyl alcohol and pantothenyl ethyl ether) may also be used as oil-soluble vitamins in the present invention. The useful vitamins may be obtained by conventional methods (e.g., a microbial transformation method, a purification method from a microbial culture and an enzymatic or a chemical synthesis method).

Any high-molecular peptides may be used as long as they may be added to cosmetics and preferably comprise collagen, hydrolyzed collagen, gelatin, elastin, hydrolyzed elastin, keratin, etc. The high-molecular peptides may be obtained by conventional methods such as a purification method from a culture medium of microorganisms, an enzymatic method, or chemical synthesis method, or may conventionally be obtained by purification from natural products such as pig's or cow's dermis or silkworm silk fibers.

Any high-molecular polysaccharides may be used as long as they may be added to cosmetics and preferably comprise hydroxyethyl cellulose, xanthan gum, sodium hyaluronate, chondroitin sulfate or a salt thereof (e.g., a sodium salt). For example, chondroitin sulfate or a salt thereof may conventionally be obtained by purification from mammals or fish.

Any sphingolipids may be used as long as they be added to cosmetics and preferably comprise ceramide, phytosphingosine, sphingoglycolipid, etc. Sphingolipids may be purified from mammals, fish, shellfish, yeasts or plants by conventional methods or obtained by a chemical synthesis method.

The cosmetic composition of the present invention may comprise other ingredients commonly added to cosmetics as needed, in addition to the above-described essential ingredients.

Other ingredients that may be added comprise oil and fat components, moisturizers, emollients, surfactants, organic or inorganic pigments, organic powders, ultraviolet absorbers, preservatives, bactericides, antioxidants, plant extracts, pH adjusters, alcohols, pigments, fragrances, blood circulation accelerators, cooling agents, antiperspirants, purified water, etc.

The oil and fat components may comprise ester-based oil and fat, hydrocarbon-based oil and fat, silicone-based oil and fat, fluorine-based oil and fat, animal oil and fat, vegetable oil and fat, etc.

The ester oil and fat may comprise glyceryl tri-2-ethylhexanoate, cetyl 2-ethylhexanoate, isopropyl myristate, butyl myristate, isopropyl palmitate, ethyl stearate, octyl palmitate, isocetyl isostearate, butyl stearate, ethyl linoleate, isopropyl linoleate, ethyl oleate, isocetyl myristate, isostearyl myristate, isostearyl palmitate, octyldodecyl myristate, isocetyl isostearate, diethyl sebacate, diisopropyl adipate, isoalkyl neopentanoate, glyceryl tri(capryl or caprylate), trimethylolpropane tri(2-ethylhexanoate), trimethylolpropane triisostearate, pentaerythritol tetra(2-ethylhexanoate), cetyl caprylate, decyl laurate, hexyl laurate, decyl myristate, myristyl myristate, cetyl myristate, stearyl stearate, decyl oleate, cetyl ricinoleate, isostearyl laurate, isotridecyl myristate, isocetyl palmitate, octyl stearate, isocetyl stearate, isodecyl oleate, octyldodecyl oleate, octyldodecyl linoleate, isopropyl isostearate, cetostearyl 2-ethylhexanoate, stearyl 2-ethylhexanonate, hexyl isostearate, ethylene glycol dioctanoate, ethylene glycol dioleate, propylene glycol dicaprate, propylene glycol di(capryl or capric), propylene glycol dicaprylate, neopentyl glycol dicaprate, neopentyl glycol dioctanoate, glyceryl tricaprylate, glyceryl triundecylate, glyceryl triisopalmitate, glyceryl triisostearate, octyldodecyl neopentanoate, isostearyl octanoate, octyl isononanoate, hexyldecyl neodecanoate, octyldodecyl neodecanoate, isocetyl isostearate, isostearyl isostearate, octyldecyl isostearate, polyglycerine oleic acid ester, polyglycerin isostearic acid ester, triisocetyl citrate, triisoalkyl citrate, triisooctyl citrate, lauryl lactate, myristyl lactate, cetyl lactate, octyldecyl lactate, triethyl citrate, acetyltriethyl citrate, acetyltributyl citrate, trioctyl citrate, diisostearyl malate, 2-ethylhexyl hydroxystearate, di(2-ethylhexyl) succinate, diisobutyl adipate, diisopropyl sebacinate, dioctyl sebacinate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stearoylhydroxystearate, stearyl 12-stearoylhydroxystearate, isostearyl 12-stearoylhydroxystearate, etc.

The hydrocarbon-based oil and fat may comprise squalene, liquid paraffin, alpha-olefin oligomer, isoparaffin, ceresin, paraffin, liquid isoparaffin, polybuden, microcrystalline wax, vaseline, etc.

Silicone-based oil and fat may comprise polymethylsilicone, methylphenylsilicone, methylcyclopolysiloxane, octamethylpolysiloxane, decamethylpolysiloxane, dodecamethylcyclosiloxane, dimethylsiloxane/methylcetyloxysiloxane copolymer, dimethylsiloxane/methylstealoxysiloxane copolymer, alkyl-modified silicone oil, amino-modified silicone oil, etc.

The fluorine-based oil and fat may comprise perfluoropolyether, etc.

The animal or vegetable oil and fat may comprise avocado oil, almond oil, olive oil, sesame oil, rice bran oil, safflower oil, soybean oil, corn oil, rapeseed oil, apricot seed oil, palm kernels oil, palm oil, castor oil, sunflower oil, grapeseed oil, cottonseed oil, coconut oil, kukui nut oil, wheat germ oil, rice germ oil, shea butter, evening primrose oil, macadamia nut oil, meadowfoam seed oil, egg yolk oil, beef tallow, horse oil, mink oil, orange roughy oil, jojoba oil, candelilla wax, carnauba wax, liquid lanolin, hydrogenated castor oil, etc.

The wetting agent may comprise a water-soluble low-molecular moisturizer, a fat-soluble molecular moisturizer, a water-soluble polymer, or an oil-soluble polymer.

The water-soluble low-molecular moisturizer may comprise serine, glutamine, sorbitol, mannitol, pyrrolidone-sodium carboxylate, glycerin, propylene glycol, 1,3-butylene glycol, ethylene glycol, polyethylene glycol B (polymerization degree n=2 or more), polypropylene glycol (polymerization degree n=2 or more), polyglycerol B (polymerization degree n=2 or more), lactic acid, lactate, etc.

The fat-soluble low-molecular moisturizer may comprise cholesterol, cholesterol ester, etc.

The water-soluble polymer may comprise carboxyvinyl polymer, polyaspartate, tragacanth, xanthan gum, methyl cellulose, hydroxymethyl cellulose, hydroxyethyl cellulose, hydroxypropyl cellulose, carboxymethyl cellulose, water-soluble chitin, chitosan, dextrin, etc.

The fat-soluble polymer may comprise polyvinylpyrrolidone/eicosene copolymer, polyvinylpyrrolidone/hexadecene copolymer, nitrocellulose, dextrin fatty acid ester, high-molecular silicone, etc.

The emollients may comprise long-chain acyl glutamic acid cholesteryl ester, cholesteryl hydroxystearate, 12-hydroxystearate, stearic acid, rosin acid, lanolin fatty acid cholesteryl ester, etc.

The surfactants may comprise nonionic surfactants, anionic surfactants, cationic surfactants, amphoteric surfactants, etc.

The nonionic surfactants may comprise self-emulsifying glycerin monostearate, propylene glycol fatty acid ester, glycerin fatty acid ester, polyglycerin fatty acid ester, sorbitan fatty acid ester, polyoxyethylene (POE) sorbitan fatty acid ester, POE sorbitan fatty acid ester, POE glycerin fatty acid ester, POE alkyl ether, POE fatty acid ester, POE hydrogenated castor oil, POE castor oil, POE/POP (polyoxyethylene/polyoxypropylene) copolymer, POE/POP alkyl ether, polyether modified silicone, lauric acid alkanolamides, alkylamine oxides, hydrogenated soybean phospholipids, etc.

The anionic surfactants may comprise fatty acid soaps, alpha-acyl sulfonates, alkyl sulfonates, alkyl allyl sulfonates, alkyl naphthalene sulfonates, alkyl sulfates, POE alkyl ether sulfates, alkyl amide sulfates, alkyl phosphates, POE alkyl phosphates, alkyl amide phosphates, alkyloylalkyl taurates, N-acyl amino acid salt, POE alkyl ether carboxylate, alkyl sulfosuccinate, sodium alkyl sulfoacetate, acylated hydrolyzed collagen peptide salt, perfluoroalkyl phosphate esters, etc.

The cationic surfactants may comprise alkyltrimethylammonium chloride, stearyltrimethylammonium chloride, stearyltrimethylammonium bromide, cetostearyltrimethylammonium chloride, distearyldimethylammonium chloride, stearyldimethylbenzylammonium chloride, behenyltrimethylammonium bromide, benzalkonium chloride, diethylaminoethyl stearate, dimethylaminopropyl stearate, quaternary ammonium salt of lanolin derivatives, etc.

The amphoteric surfactants may comprise carboxybetaine type, amidebetaine type, sulfobetaine type, hydroxysulfobetaine type, amide sulfobetaine type, phosphobetaine type, aminocarboxylate type, imidazoline derivative type, amideamine type, etc.

The organic or inorganic pigments may comprise inorganic pigments (e.g., silicic acid, silicic anhydride, magnesium silicate, talc, sericite, mica, kaolin, bengala, clay, bentonite, titanium-coated mica, bismuth oxychloride, zirconium oxide, magnesium oxide, zinc oxide, titanium oxide, aluminum oxide, calcium sulfate, barium sulfate, magnesium sulfate, calcium carbonate, magnesium carbonate, iron oxide, ultramarine blue, chromium oxide, chromium hydroxide, calamine and complexes thereof); organic pigments (e.g., polyamide, polyester, polypropylene, polystyrene, polyurethane, vinyl resin, urea resin, phenolic resin, fluororesin, silicon resin, acrylic resin, melamine resin, epoxy resin, polycarbonate resin, divinylbenzene/styrene copolymer, silk powder, cellulose, CI pigment yellow and CI pigment orange); and complex pigments of inorganic pigments and organic pigments thereof.

The organic powders may comprise metal soaps such as calcium stearate; alkyl phosphate metal salt (e.g., zinc sodium cetylrate, zinc laurylrate and calcium laurylrate); polyvalent metal salt of acyl amino acids (e.g., N-lauroyl-beta-alanine calcium, N-lauroyl-beta-alanine zinc and N-lauroyl glycine calcium); polyvalent metal salt of amide sulfonic acids (e.g., N-lauroyl-taurine calcium and N-palmitoyl-taurine calcium); acyl basic amino acids (e.g., N-epsilon-lauroyl-L-lysine, N-epsilon-palmitoylizine, N-alpha-paritoylolnithine, N-alpha-lauroylarginine and N-alpha-hardened tallow fatty acid acylarginine); N-acyl polypeptides such as N-lauroylglycylglycine; alpha-amino fatty acids such as alpha-aminocaprylic acid and alpha-aminolauric acid; polyethylene, polypropylene, nylon, polymethyl methacrylate, polystyrene, divinylbenzene/styrene copolymer, tetrafluoroethylene, etc.

The UV absorbers may comprise para-aminobenzoic acid, ethyl para-aminobenzoate, amyl para-aminobenzoate, octyl para-aminobenzoate, ethylene glycol salicylate, phenyl salicylate, octyl salicylate, benzyl salicylate, butylphenyl salicylate, homomenthyl salicylate, benzyl cinnamate, 2-ethoxyethyl p-methoxycinnamate, octyl p-methoxycinnamate, glyceryl mono-2-ethylhexane di-p-methoxycinnamate, isopropyl p-methoxycinnamate, diisopropyl/diisopropylcinnamate ester mixture, ethyl urocanate, hydroxymethoxybenzophenone, hydroxymethoxybenzophenonesulfonic acid and its salt, dihydroxymethoxybenzophenone, sodium dihydroxymethoxybenzophenone disulfonate, dihydroxybenzophenone, tetrahydroxybenzophenone, 4-tert-butyl-4'-methoxydibenzoylmethane, 2,4,6-trianilino-p-(carbo-2'-ethylhexyl-1'-oxy)-1,3,5-triazine, 2-(2-hydroxy-5-methylphenyl)benzotriazole, etc.

The bactericides may comprise hinokitiol, triclosan, trichlorohydroxydiphenyl ether, chlorhexidine gluconate, phenoxyethanol, resorcin, isopropylmethylphenol, azulene, salicylic acid, zincphyllione, benzalkonium chloride, photosensitizer No. 301, mononitro guaiacol sodium, undecylenic acid, etc.

The antioxidants may comprise butylhydroxyanisole, propyl gallic acid, erythorbic acid, etc.

The pH adjusters may comprise citric acid, sodium citrate, malic acid, sodium malate, fumaric acid, sodium fumarate, succinic acid, sodium succinate, sodium hydroxide, sodium monohydrogen phosphate, etc.

The alcohols may comprise higher alcohols such as cetyl alcohol.

In addition, the ingredients that may be added are not limited to the above-described composition, and any of the above ingredients may be employed within a range that does not impair the object and effect of the present invention, provided that they are employed in an amount of preferably 0.01 to 5% by weight, more preferably 0.01 to 3% by weight, based on the total weight of the composition.

When the formulation of the present invention is a lotion, a paste, a cream or a gel, the carrier components may comprise an animal fiber, a vegetable fiber, a wax, a paraffin, a starch, tracanth, cellulose derivatives, polyethylene glycol, silicone, bentonite, silica, talc, zinc oxide, etc.

When the formulation of the present invention is a powder or a spray, the carrier components may comprise lactose, talc, silica, aluminum hydroxide, calcium silicate or polyamide powder, and, in particular, when the formation of the present invention is a spray, the carrier components may additionally comprise a propellant (e.g., chlorofluorohydrocarbon, propane/butane or dimethyl ether).

When the formulation of the present invention is a solution or an emulsion, the carrier components may comprise a solvent, a solvating agent or an emulsifying agent, for example, water, ethanol, isopropanol, ethyl carbonate, ethyl acetate, benzyl alcohol, benzyl benzoate, propylene glycol, 1,3-butyl glycol oil, glycerol aliphatic esters, polyethylene glycol or sorbitan esters of fatty acids.

When the formulation of the present invention is a suspension, the carrier components may comprise a liquid diluent (e.g., water, ethanol or propylene glycol), a suspending agent (e.g., an ethoxylated isostearyl alcohol, polyoxyethylene sorbitol ester and polyoxyethylene sorbitan ester), microcrystalline cellulose, aluminum metahydroxide, bentonite, agar, tracanth, etc.

When the formulation of the present invention is a surfactant-containing cleansing agent, the carrier components may comprise aliphatic alcohol sulfate, aliphatic alcohol ether sulfate, sulfosuccinic acid monoester, isethionate, imidazolinium derivatives, methyl taurate, sarcosinate, fatty acid amide ether sulfates, alkylamidobetaines, aliphatic alcohols, fatty acid glycerides, fatty acid diethanolamides, vegetable oils, linolin derivatives, ethoxylated glycerol fatty acid esters, etc.

Hereinafter, the present invention will be described in more detail through working examples. The following examples are merely examples to aid understanding of the present invention, and the scope of the present invention is not limited thereto.

EMBODIMENT

Experimental Example 1. Measurement of the Activities of the Epidermal Growth Factor Receptor (EGFR) of Isoprocurcumenol Phosphorylation of tyrosine residues present in the cytoplasmic portion of the EGFR as the EGF receptor of the cell membrane occurs accompanied by activation of the EGFR. In addition, by using the feature that, when the activities of the EGFR continue to be maintained, the EGFR is internalized into the cell, the cell of the biosensor system that may measure the activities of the EGFR was used in the present experimentation (see Korean Laid-open Patent Publication No. 2019-0014340).

The cells of the biosensor system were treated with 10 ng/ml of an EGF and 100 μM of Isoprocurcumenol (purchased from InterPharm), and changes in fluorescence signals were observed. After culturing the cells in a serum-free medium for 24 hours, the cells were treated with Isoprocurcumenol.

As a result, as shown in FIG. 1, it was confirmed that the EGFR was activated in the cells treated with 100 μM of Isoprocurcumenol as compared to the control group treated only with the solvent DMSO.

Experimental Example 2. Measurement of Cytotoxicity Depending on the Concentrations of Isoprocurcumenol The cytotoxicity of Isoprocurcumenol was measured using HaCaT cells as keratinocytes.

When cells are treated with MTT tetrazolium which is a yellow water-soluble substrate, such a substrate is reduced to MTT formazan by mitochondrial enzymes, and the color changes to blue-purple. That is, since the blue-violet color appears darker as the number of living cells increases, the blue-violet absorbance at a wavelength of 540 nm reflects the concentration of living cells.

Specifically, after culturing cells to fill each well of a 96-well plate, the cells were treated with Isoprocurcumenol at concentrations of 0, 10, 25, 50 and 100 μM, and cultured for 24 hours and 48 hours in a 5% CO2 incubator at 37° C. Thereafter, cell viability was measured using MTT reagent. A control group not treated with Isoprocurcumenol (0 μM) was treated with the same amount of the solvent DMSO.

As a result, as shown in FIG. 2, it was confirmed that, when the cells were cultured for 48 hours with 100 μM of Isoprocurcumenol, some cytotoxicity was shown, and the difference was as slight as 10%. As such, it was confirmed that the cytotoxicity in keratinocytes was very low.

Experimental Example 3. The Activities of ERK and AKT by Isoprocurcumenol

It is well known that the activities of extracellular signal-regulated kinase (ERK) and protein kinase B (AKT) transmit signals necessary for cell growth and survival by the activities of an EGFR. In addition, in Experimental Example 1, it was observed that Isoprocurcumenol generated signals due to activation of the EGFR in the cells of the biosense system for measuring the activities of the EGFR. Accordingly, it was measured whether the activities of the EGFR were induced by Isoprocurcumenol to the activities of the ERK and AKT.

Specifically, HaCaT cells were cultured in a serum-free medium, treated with 10 μM of Isoprocurcumenol for 10 minutes, 30 minutes and 60 minutes, respectively, and, thereafter, phosphorylated and activated ERK and AKT were analyzed by Western blotting. As antibodies, a phosphorylation antibody as a marker of activated ERK and AKT, and a general antibody for measuring all thereof were used, respectively.

Figure 3:
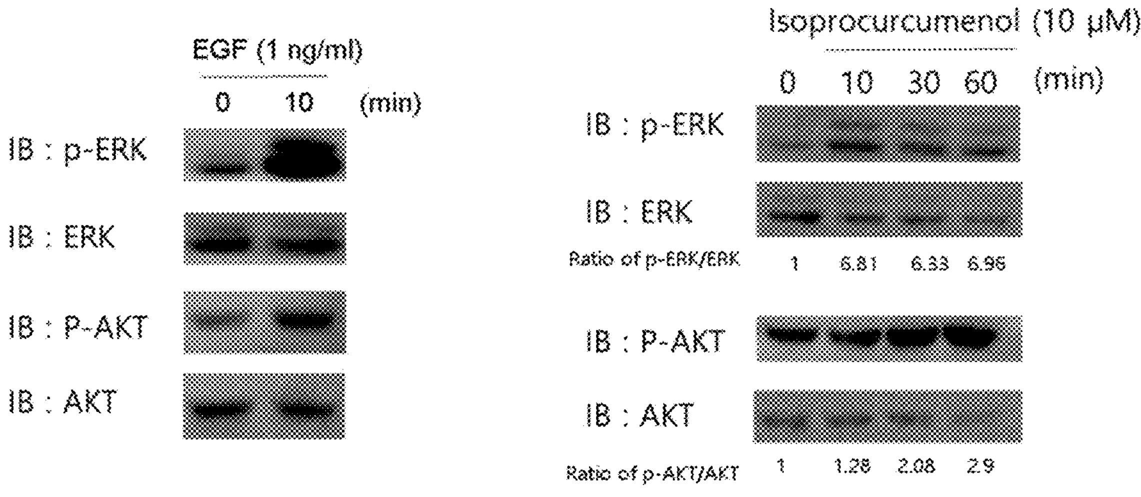
FIG. 3 shows the results of confirming that ERK and AKT as subtypes of an EGFR were activated by Isoprocurcumenol.

As a result, as shown in FIG. 3, it was confirmed that 10 μM of Isoprocurcumenol sufficiently induced the activities of the ERK and AKT for 10 minutes. It was also confirmed that the ERK and AKT were rapidly activated within 30 minutes.

Experimental Example 4. Changes in Gene Expression by Isoprocurcumenol

Signaling by an EGFR induces the expression of genes important for cell growth and survival through important signaling mediator proteins such as ERK and AKT. The egr1, c-myc, c-jun and c-fos genes are regulated by the EGFR and are well known as genes that promote cell growth and survival. In Experimental Example 2, HaCaT cells cultured in a serum-free medium were treated with Isoprocurcumenol which sufficiently induced the activities of the ERK and AKT, at a concentration of 10 μM, and 1 hour later, each gene expression change was analyzed.

Specifically, Tri-reagent was used for mRNA extraction, cDNA was created by a reverse transcription polymerase chain reaction (RT-PCR) using a poly-A primer and a reverse transcriptase, and real-time quantitative PCR was used to measure the amount of each mRNA. The amount of each mRNA was corrected with the amount of β-actin, which is a constitutive gene.

Figure 4:
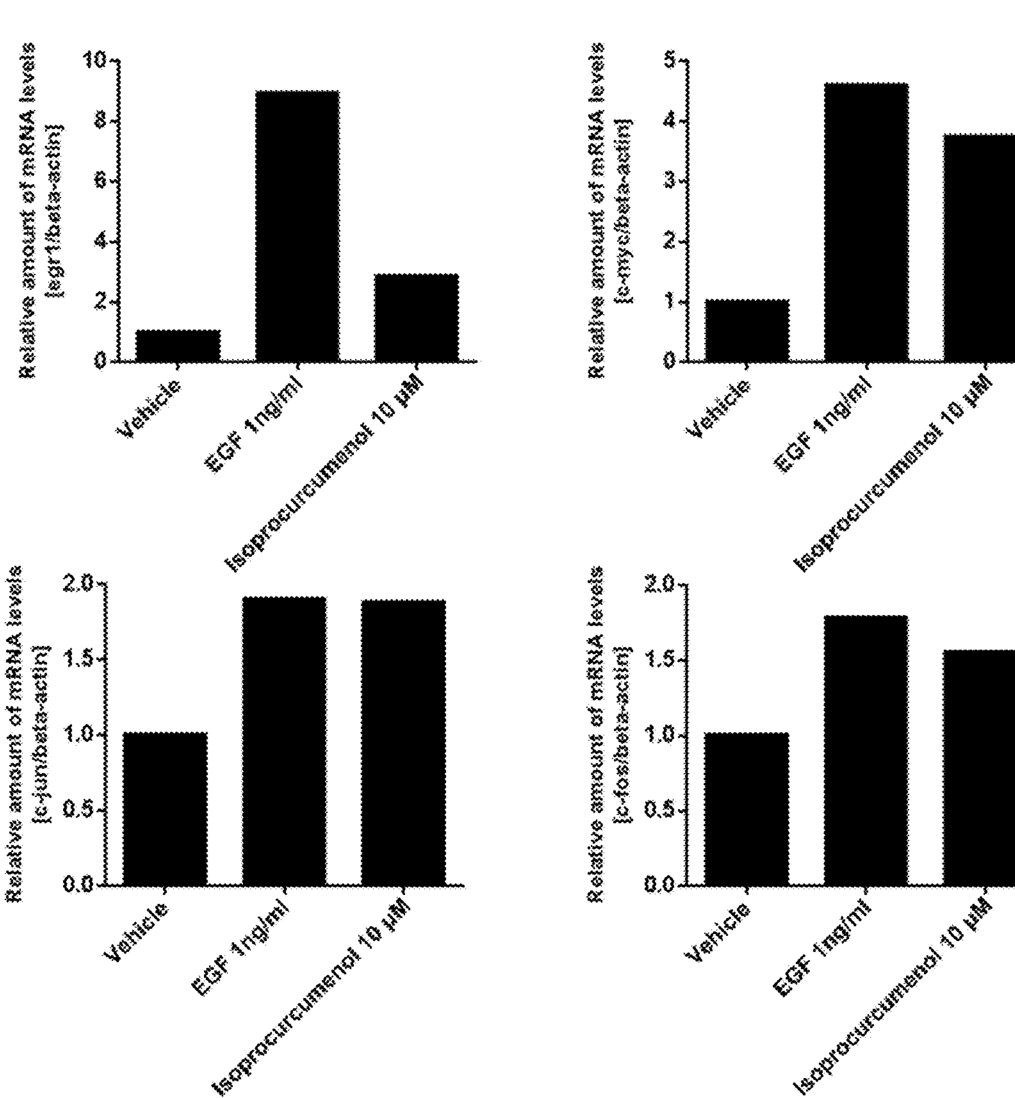
FIG. 4 shows the results of confirming expression patterns of egr1, c-myc, c-jun, and c-fos genes increased by Isoprocurcumenol.

As a result, as shown in FIG. 4, egr1, c-myc, c-jun and c-fos mRNA increased.

Experimental Example 5. Measurement of Growth and Proliferation of Keratinocytes by Isoprocurcumenol Cell counting kit-8 (CCK-8) is a water-soluble tetrazolium salt reagent called WST-8 and forms orange-colored water-soluble Formazan by dehydrogenase in the mitochondria of living cells. As such, the absorbance at 450 nm, which is an orange-colored wavelength exhibited by CCK-8, reflects the number of cells and, thus, was used to measure the growth and proliferation of the cells. The growth promotion effects of HaCaT cells as keratinocytes were measured by using Isoprocurcumenol free of cytotoxicity at the concentration of 10 μM or less, i.e., 1 nM, 10 nM, 100 nM, 1 μM and 10 μM, through the CCK-8 assay.

Specifically, after culturing $1\times10^4$ HaCaT cells in a 96-well plate for 24 hours, the cells were changed to a serum-free medium to remove the growth factors contained in the medium, and treated with Isoprocurcumenol at the concentrations of 1 nM, 10 nM, 100 nM, 1 μM and 10 μM. As a negative control group, the same amount of the solvent DMSO was used, and, as a positive control group, an EGF at a concentration of 1 ng/ml was used. After cultured for 24 hours, the cells were treated with CCK8, and the cell growth was analyzed by measuring absorbance at 450 nm.

Figure 5:
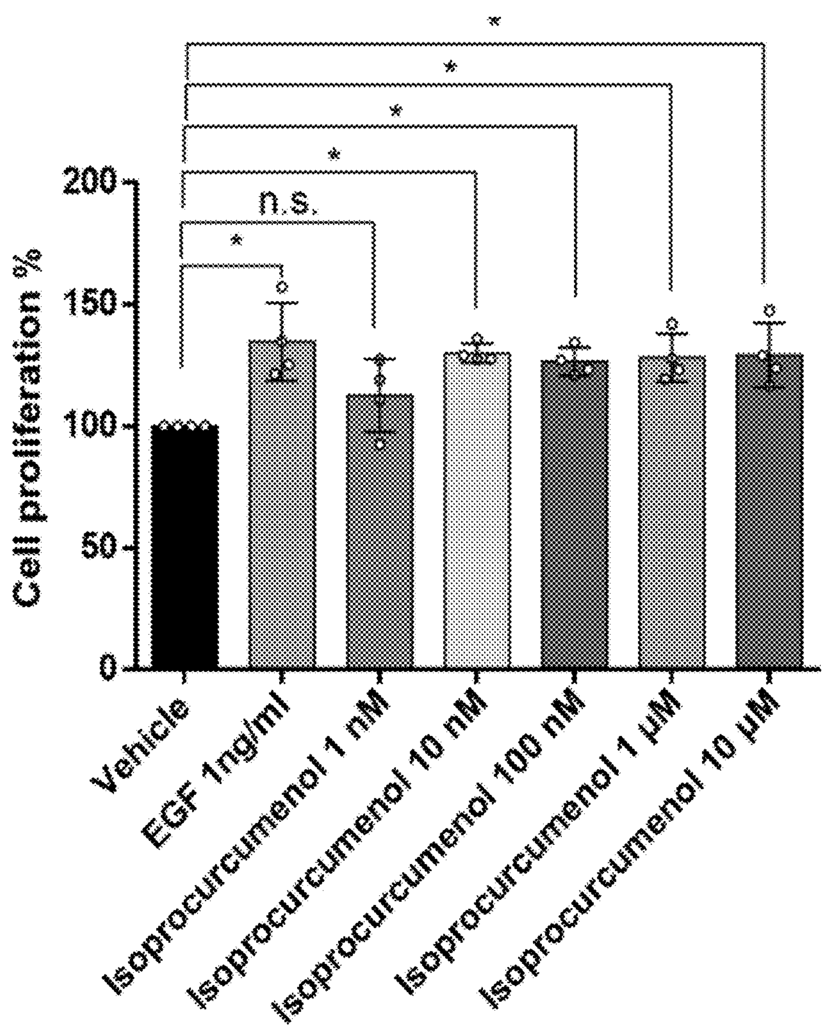
FIG. 5 shows the results of confirming the growth promotion effects of keratinocytes by Isoprocurcumenol, through CCK-8 assays.

As a result, as shown in FIG. 5, it was confirmed that, when the cells were treated with 10 nM, 100 nM, 1 μM, and 10 μM concentrations of Isoprocurcumenol, the growth and proliferation of cells significantly increased as compared to the negative control group (One-way ANOVA, $*p<0.05$).

Experimental Example 6. Cell Growth Promotion Effect by Isoprocurcumenol

The cell growth promoting effect of Isoprocurcumenol was confirmed through wound healing assay. Specifically, after fully culturing HaCaT cells in a 12-well plate, cells on a certain area were scraped off using a yellow tip to form a wound area, changed to a serum-free medium, and treated with 1 μM of Isoprocurcumenol. As the negative control group, the solvent DMSO was used, and, as the positive control group, 1 ng/ml of EGF was used.

Figure 6A:
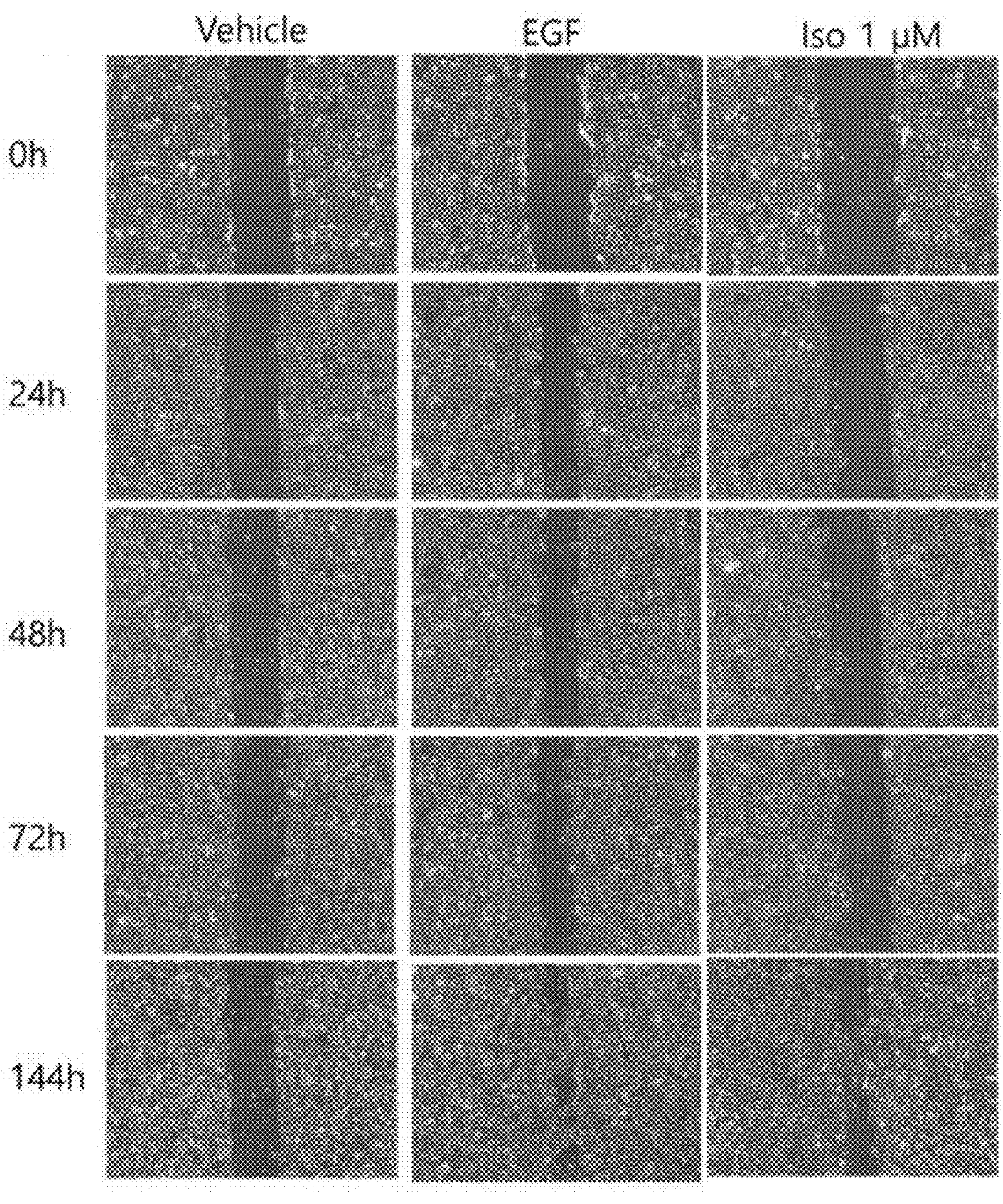
FIGS. 6*a* and 6*b* respectively show a photograph and a graph showing the results of confirming the proliferation and growth promotion effects of keratinocytes by Isoprocurcumenol, through Wound healing assay.
Figure 6B:
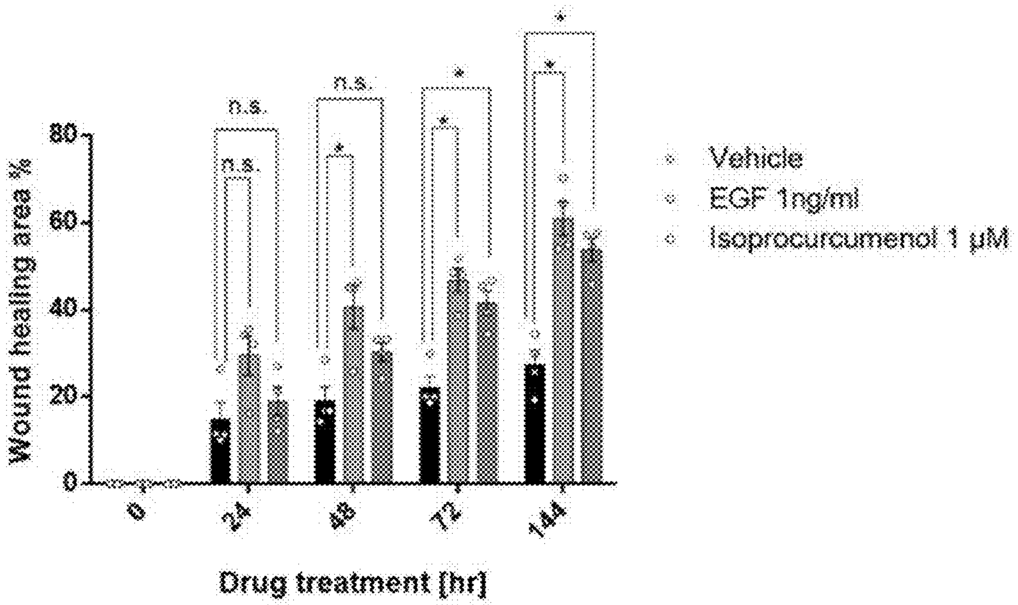

As a result, as shown in FIGS. 6A and 6B, it was confirmed that, when Isoprocurcumenol was treated during culture for 6 days, the wound area was more quickly filled as compared to the negative control group and, from the 3rd day, showed a more significant difference as compared to the negative control group. (t-test, $*p<0.05$).

Experimental Example 7. Efficacy of Isoprocurcumenol on Resistance to Ultraviolet (UVB) Stimulation Among the ultraviolet wavelengths, UVB wavelengths corresponding to 280 to 315 nm penetrate the epidermal layer where many keratinocytes exist to cause cell damage. Since the cell damage caused by UVB also leads to apoptosis, it was confirmed whether or not Isoprocurcumenol exhibits resistance to cell damage induced by UVB as it promotes the transmission of the growth and survival signals of the keratinocytes.

Specifically, a 96-well plate in which $1\times10^4$ HaCaT cells were cultured was irradiated with 500 mJ/cm2 of UVB and then cultured in a serum-free medium comprising Isoprocurcumenol or EGF at a concentration of 1 μM. The solvent DMSO was used as a negative control group, and the cell viability was measured using the CCK-8 method used in Experimental Example 6.

Figure 7:
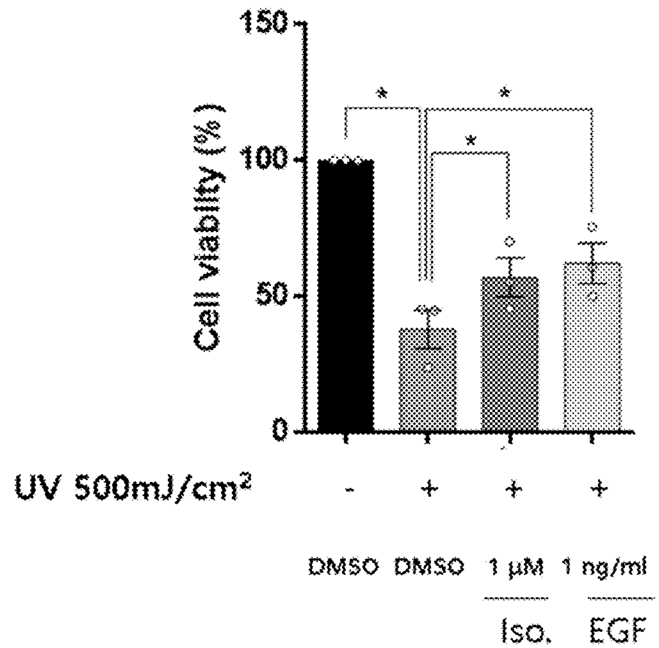
FIG. 7 shows that the resistance of keratinocytes increases due to Isoprocurcumenol (Iso.) under conditions of cell damage caused by UVB.

As a result, as shown in FIG. 7, it was confirmed that apoptosis was caused by UVB at 500 mJ/cm2 in the negative control group such that only about 40% of cells survived, whereas about 60% of cells survived by 1 μM of Isoprocurcumenol, which showed a statistically significant value. (t-test, $*p<0.05$).

INDUSTRIAL APPLICABILITY

While example embodiments have been shown and described above, it will be apparent to those skilled in the art that modifications and variations could be made without departing from the scope of the present disclosure as defined by the appended claims.

The invention claimed is:

1. A method for skin regeneration by improving or treating skin, tissue, or cell damage, comprising administering to a subject in need thereof a composition comprising isoprocurcumenol having the following formula (1) in an amount of 10 nM to 50 μM:

[Formula (1)]

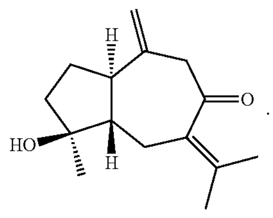

2. The method according to claim 1, wherein the subject requires improving or treating skin and tissue damage caused by burns.

3. The method according to claim 1, wherein the subject requires improving cell damage from external stimuli.

4. The method according to claim 3, wherein the external stimuli are ultraviolet rays.

5. The method according to claim 1, wherein the subject requires enhancing skin elasticity.

6. The method according to claim 1, wherein the subject requires improving a problem of skin wrinkles.

7. The method according to claim 1, wherein the composition is a pharmaceutical composition, a health functional food composition or a cosmetic composition.

* * * * *